United States Patent [19]

Seymour

[11] Patent Number: 5,260,031
[45] Date of Patent: Nov. 9, 1993

[54] SALIVA SAMPLING DEVICE WITH SAMPLE ADEQUACY INDICATING SYSTEM

[75] Inventor: Eugene H. Seymour, Pacific Palisades, Calif.

[73] Assignee: Saliva Diagnostic Systems, Inc., Vancouver, Wash.

[21] Appl. No.: 831,776

[22] Filed: Feb. 5, 1992

Related U.S. Application Data

[63] Continuation-in-part of Ser. No. 629,278, Dec. 18, 1990, abandoned, and a continuation-in-part of Ser. No. 722,333, Jun. 25, 1991, abandoned.

[51] Int. Cl.$^5$ .................. G01N 33/48; C12M 1/30; C12M 1/28
[52] U.S. Cl. .................. 422/101; 128/760; 422/58; 422/99; 422/102
[58] Field of Search .............. 128/632, 670, 762, 769; 422/58, 99–102; 435/295, 294

[56] References Cited

U.S. PATENT DOCUMENTS

| | | | |
|---|---|---|---|
| 3,086,527 | 4/1963 | Forrest | 128/760 X |
| 3,117,569 | 1/1964 | Wegner | 604/1 X |
| 3,163,160 | 12/1964 | Cohen | 604/1 X |
| 3,773,035 | 11/1973 | Aronoff | 604/1 X |
| 3,776,220 | 12/1973 | Monaghan | 128/2 W |
| 3,783,104 | 1/1974 | Henshilwood et al. | 435/295 X |
| 3,815,580 | 6/1974 | Oster | 604/1 X |
| 3,832,141 | 8/1974 | Haldopoulos | 422/102 X |
| 3,846,077 | 11/1974 | Ohringer | 422/102 X |
| 3,890,954 | 6/1975 | Greenspan | 604/1 X |
| 3,913,562 | 10/1975 | Moore et al. | 435/295 |
| 3,913,564 | 10/1975 | Freshley | 604/1 |
| 3,918,435 | 11/1975 | Beall | 128/2 W |
| 3,924,607 | 12/1975 | Bucalo | 128/769 X |
| 3,939,044 | 2/1976 | Wilkins et al. | 435/295 |
| 3,954,563 | 5/1976 | Mennen | 435/292 |
| 3,966,558 | 6/1976 | Calva-Pellicer | 435/295 |
| 4,014,322 | 3/1977 | Shah | 128/760 |
| 4,014,746 | 3/1977 | Greenspan | 604/1 |
| 4,057,499 | 11/1977 | Buono | 422/101 X |
| 4,070,249 | 1/1978 | Janin et al. | 422/102 |
| 4,073,693 | 2/1978 | Janin | 195/103.5 |
| 4,150,950 | 4/1979 | Takeguchi et al. | 422/102 X |
| 4,159,193 | 6/1979 | Gauntley et al. | 422/101 |
| 4,163,039 | 7/1979 | Emrich | 422/58 X |
| 4,175,008 | 11/1979 | White | 435/295 |
| 4,175,439 | 11/1979 | Laker | 604/1 X |
| 4,184,483 | 1/1980 | Greenspan | 435/295 |
| 4,223,093 | 9/1980 | Newman et al. | 435/295 |
| 4,268,270 | 5/1981 | Gabbay et al. | 422/58 X |
| 4,308,028 | 12/1981 | Elkins | 422/58 X |
| 4,311,792 | 1/1982 | Avery | 435/30 |
| 4,353,868 | 10/1982 | Joalin et al. | 422/101 |
| 4,387,725 | 6/1983 | Mull | 435/295 |
| 4,409,988 | 10/1983 | Greenspan | 128/759 |
| 4,418,702 | 12/1983 | Brown et al. | 422/102 |
| 4,444,193 | 4/1984 | Fogt et al. | 422/58 X |
| 4,492,305 | 1/1985 | Avery | 435/295 |
| 4,578,588 | 3/1986 | Galkin | 422/102 X |
| 4,604,360 | 8/1986 | Hounsell | 435/287 |
| 4,624,929 | 11/1986 | Ullman | 422/100 X |
| 4,635,488 | 1/1987 | Kremer | 128/760 X |
| 4,657,869 | 4/1987 | Richards et al. | 435/287 |
| 4,707,450 | 11/1987 | Nason | 435/295 |
| 4,717,661 | 1/1988 | McCormick et al. | 435/31 |
| 4,741,346 | 5/1988 | Wong | 128/760 |
| 4,743,537 | 5/1988 | McCormick et al. | 435/295 |
| 4,747,719 | 5/1988 | Parkin | 604/1 X |
| 4,749,655 | 6/1988 | Monthony | 435/295 |
| 4,770,853 | 9/1988 | Bernstein | 422/58 |
| 4,774,962 | 10/1988 | Hebel et al. | 128/760 |
| 4,777,964 | 10/1988 | Briggs et al. | 128/760 |

(List continued on next page.)

Primary Examiner—James C. Housel
Assistant Examiner—Arlen Soderquist
Attorney, Agent, or Firm—W. Edward Johansen

[57] ABSTRACT

A saliva sampling device includes a holder, a saliva collector and an indicator. The saliva collector selectively receive a sample of saliva. The saliva collector is a piece of filter paper and is fixed to the holder. The indicator is activated by a preselected amount of the received sample of saliva. The indicator is coupled to the holder and to the saliva collector so that a technician can collect the sample of the saliva and determine that it is of adequate amount.

2 Claims, 5 Drawing Sheets

U.S. PATENT DOCUMENTS

| | | | |
|---|---|---|---|
| 4,788,985 | 12/1988 | Manning et al. | 128/759 |
| 4,789,639 | 12/1988 | Fleming | 436/178 |
| 4,803,998 | 2/1989 | Kezes et al. | 128/759 |
| 4,813,432 | 3/1989 | Saint-Amand | 128/749 |
| 4,859,610 | 8/1989 | Maggio | 436/518 |
| 4,871,662 | 10/1989 | Rosov | 435/30 |
| 4,895,808 | 1/1990 | Romer | 422/101 X |
| 4,978,504 | 12/1990 | Nason | 422/61 |
| 5,000,193 | 3/1991 | Heelis et al. | 128/760 |
| 5,063,026 | 11/1991 | Wong | 422/102 |
| 5,078,968 | 1/1992 | Nason | 422/58 |
| 5,079,142 | 1/1992 | Coleman et al. | 422/58 X |
| 5,091,316 | 2/1992 | Monthony et al. | 435/295 |
| 5,096,062 | 3/1992 | Burkhardt et al. | 422/102 |
| 5,102,631 | 4/1992 | Jordan et al. | 422/42 |
| 5,103,836 | 4/1992 | Goldstein et al. | 128/760 |
| 5,135,873 | 8/1992 | Patel et al. | 422/100 |
| 5,188,985 | 12/1992 | Manning | 128/759 |

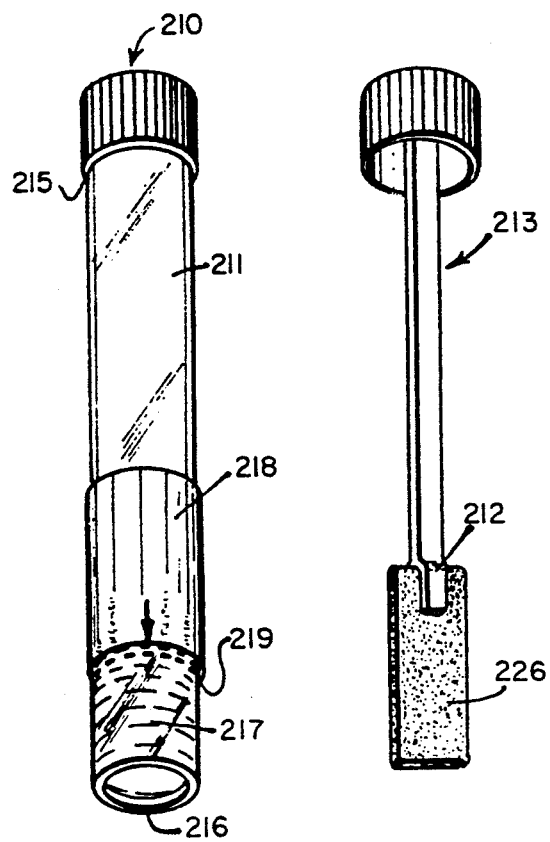
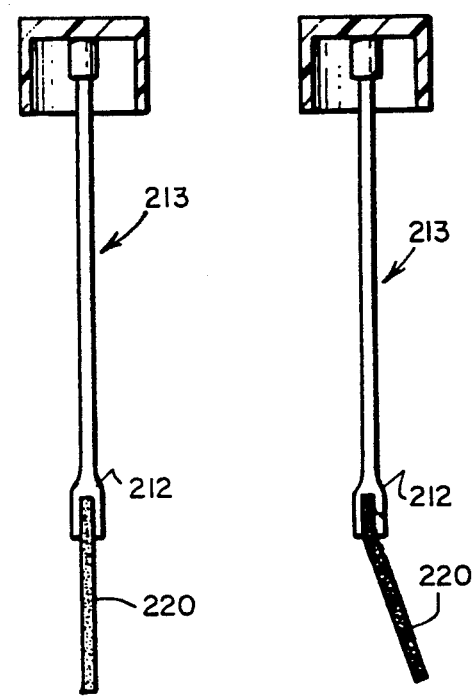
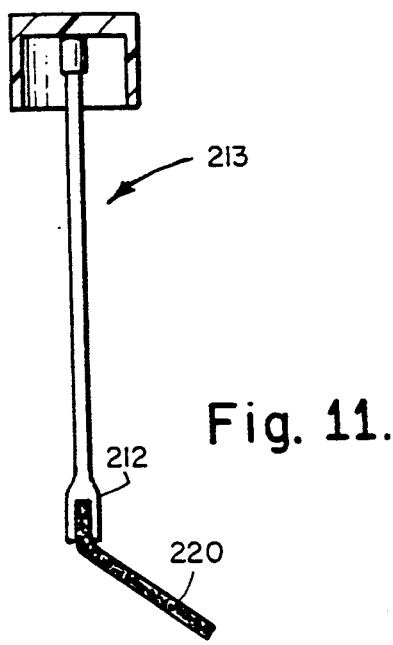
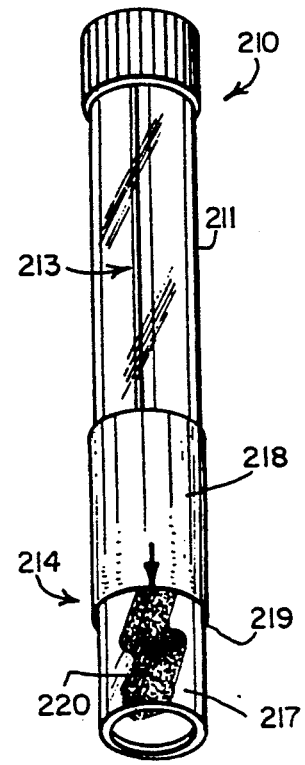
Fig. 7. Fig. 8. Fig. 9. Fig. 10. Fig. 11. Fig. 12.

Fig. 23.
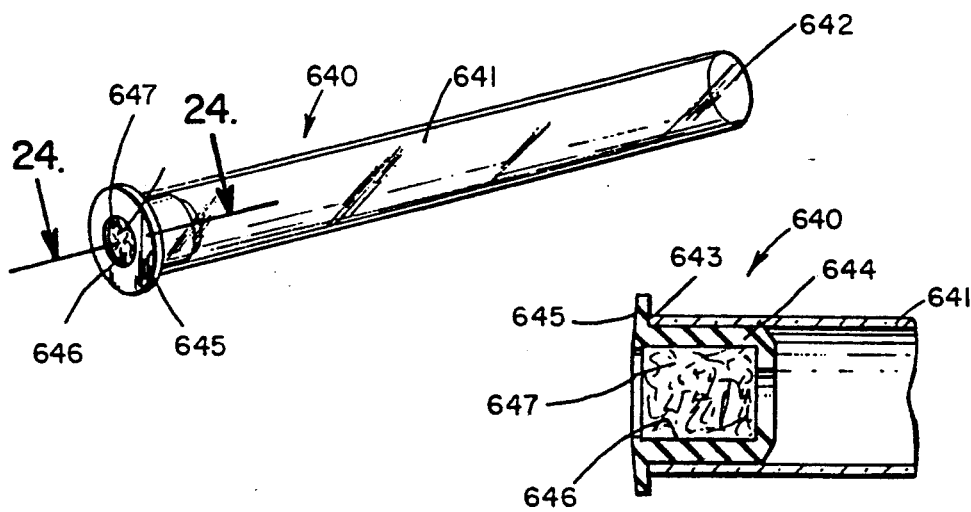
Fig. 24.
Fig. 25.
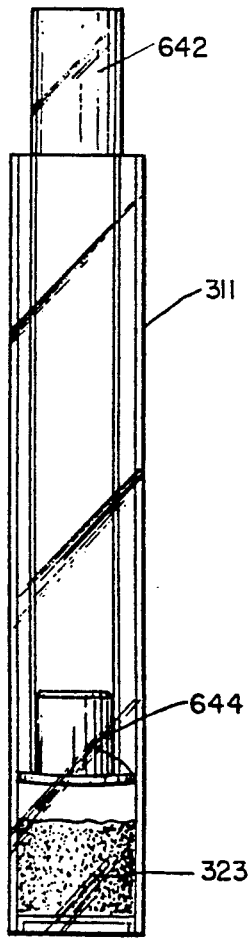
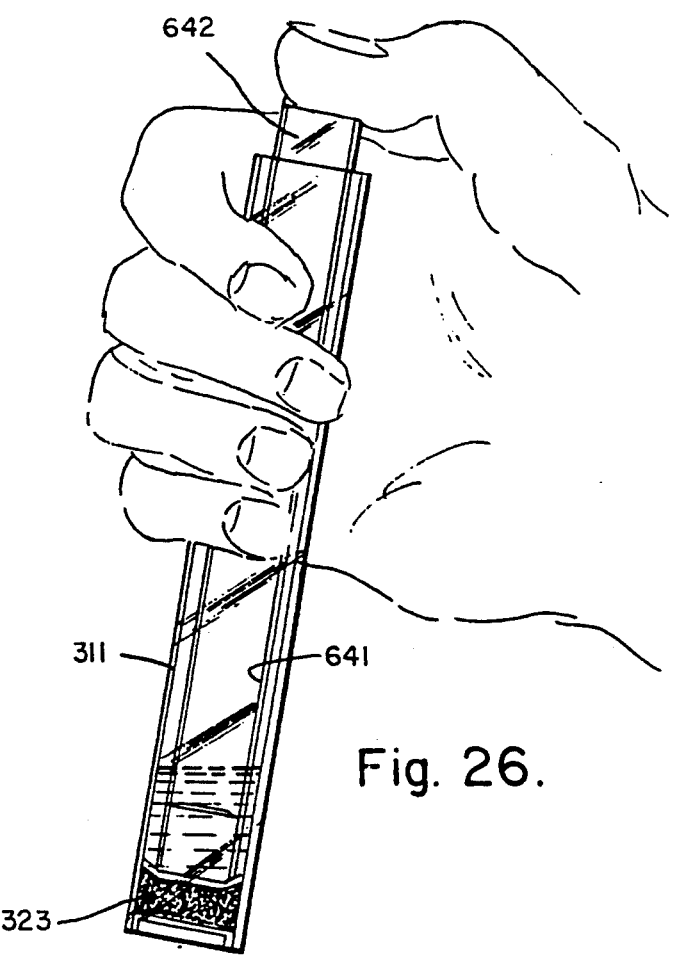
Fig. 26.

SALIVA SAMPLING DEVICE WITH SAMPLE ADEQUACY INDICATING SYSTEM

This application is a continuation-in-part of the application filed Dec. 18, 1990 under Ser. No. 629,278 and a continuation-in-part of the application filed Jun. 25, 1991 under Ser. No. 722,333, now abandoned which is a continuation-in-part of the application filed Dec. 18, 1990 under Ser. No. 629,278, now abandoned.

BACKGROUND OF THE INVENTION

1. Field of the Invention

The field of the invention is saliva sampling devices.

2. Description of the Prior Art

The current literature indicates saliva is used to conveniently, easily, safely and effectively test an individual for a variety of medical conditions. These tests for medical conditions include a hepatis screening for restaurant employees, HIV, continue (nicotine) and cocaine screening by insurance companies and a five minute HIV screening by a dentist. Clinics for oncology, neurology, infertility, allergy orthopedic and pain which had used urine, blood and serum samples to determine the medical conditions of their patients are now using samples of saliva for this same purpose.

U.S. Pat. No. 4,150,950 teaches a sampling device which includes a container, a seal, a screw-cap, an elongated element and a specimen collector. The container has a liquid reagent which the seal seals into the bottom portion thereof capable of preserving the activity of a particular specimen. The specimen collector is attachable to the inside of the screw cap through the elongated element which is of sufficient length to immerse the specimen collector into the liquid. After a specimen has been obtained, the specimen collector, which is attached to the screw cap, is forced through the seal into the liquid preservative as the screw cap is fastened tightly onto the container.

U.S. Pat. No. 4,774,962 teaches a method of extracting human saliva in which a resilient absorbent inert body is chewed by a person and is subsequently introduced into a centrifuge tubule provided with an apertured floor. The centrifuge tubule is introduced into a centrifuge and subjected to a spinning process, whereupon the saliva is pressed out of the resilient body and passes through the floor into the lower part of the centrifuge tubule.

U.S. Pat. No. 4,992,296 teaches a drug abuse test papers which are bibulous paper carriers which have been impregnated with specific test chemicals, including bismuth subnitrate, potassium iodide, acetic acid, and platinum salt, in two coatings and dried after each coating under specific temperature conditions. The test chemicals are provided for the detection of the drug abuse compounds of amphetamine, cocaine, marijuana, and narcotics contained in low concentrations in animal or human urine.

U.S. Pat. No. 4,635,488 teaches a body fluid sampling device which includes a hollow tube with a solid, porous, water-wettable nonfibrous nib mounted in and protrudes from one end of the tube for collecting, by absorption, a sample of a body fluid such as sweat, tears, or saliva. The sample may be extracted from the nib for analysis by supplying an extraction fluid to the interior of the tube for gravity. Alternatively, a strip of paper, which contains an agent that changes appearance to indicate the presence of a substance to be detected, may be disposed in the hollow tube for endwise contact with the nib to receive the sample or components thereof by absorption.

U.S. Pat. No. 4,418,702 and U.S. Pat. No. 4,580,577 teach a method for collecting saliva from a test subject which includes providing a flavored absorbent sponge for mastication and charging it with saliva and then expressing the saliva from the flavored absorbent sponge. The apparatus for this method includes a barrel-piston arrangement in association with a specimen vial for storage until diagnostic testing.

U.S. Pat. No. 4,817,632 teaches an oral fluid collection article for placement in the buccal cavity of an individual for the collection and filtering of a saliva fluid. The collection article has a semi-permeable membrane container enclosing an osmotic membrane.

U.S. Pat. No. 4,607,009 teaches an assay for determining the Lewis blood group of a patient which consists of testing a body sample for the presence of Lewis antigens. Monoclonal antibodies specific for either of these antigens are employed which do not cross-react with other related antigens. Body samples which may be tested include saliva, serum, urine, and paraffin-embedded tissue samples.

U.S. Pat. No. 4,720,455 teaches a test kit of several reagents, test tubes and a dip-stick carrying an anti-progesterone monoclonal antibody. U.S. Pat. No. 4,722,889 teaches a reagent kit is provided for assay of a selected antigen in an aliquot of body fluid.

U.S. Pat. No. 4,769,216 teaches a test kit which is used in detecting or determining the presence of antigenic or haptenic substances or antibodies in a sample. The test kit includes a plurality of tubular or capillary elements, each having antibodies or antigenic or haptenic substances attached to an internal surface thereof, and mechanism for causing fluids to pass simultaneously or sequentially through the plurality of capillary elements.

U.S. Pat. No. 4,771,486 teaches a sputum sampling device having capability for sputum-saliva separation which includes a substantially circular cup having a wall portion which tapers inwardly from top to bottom, a separation plate having a substantially elliptical planar confiuration, the major and minor axis of the plate being dimensioned to allow insertion of the plate down into the cup at a slant to position the lower portion of the plate a distance above the bottom of the cup, a plurality of apertures formed in the lower portion of the plate to provide saliva drainage ports, and an upper portion of the plate comprising a roughened textured surface for retracting and holding sputum in position for recovery in order to obtain a sensory and microbiological examination.

U.S. Pat. No. 4,853,325 teaches a saliva test for feline leukemia virus (FeLV) which includes a probe which has an immunochemically sensitive member for collecting saliva from the oral cavity of a cat. The probe employs ELISA reagents for the incubation of the probe and the development of color reactions to indicate the presence or absence of FeLV within the saliva sample collected onto the probe.

U.S. Pat. No. 4,468,470 teaches a method for the assay of antibodies to soluble antigens in an aqueous sample in body fluids, such as blood serum or blood plasma, by contacting the sample with an antigen in vitro. The antibodies, if present, are bound by the antigens.

U.S. Pat. No. 4,929,544 teaches that human cancer is diagnosed/monitored by measuring an antigen level in a physiological fluid specimen of a subject by a quantitative immunoassay. That antigen level is then compared to the antigen level of that occurs in corresponding physiological fluid of normal subjects to determine whether the former is substantially elevated over the latter.

SUMMARY OF INVENTION

The present invention is directed to a saliva sampling device having a saliva collector which selectively receives a sample of saliva and an indicator which is activated by a preselected amount of the received sample of saliva.

In another aspect of the present invention, a saliva sampling device including a wetable element and an indicator which to the wetable element and which reacts with saliva to change appearance.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE DRAWING

FIG. 7 is a perspective view of a third container of a third saliva sampling device, which includes a first sample adequacy system, in accordance with the principles of the third embodiment.

FIG. 8 is a perspective view of a third saliva collector including a third holder, a third elongated member and a third rectangular piece of filter paper in accordance with the principles of the third embodiment.

FIG. 9 is a side elevational view in cross-section of the third saliva collector of FIG. 8 before the third saliva collector has been placed in a subject's mouth.

FIG. 10 is a side elevational view in cross-section of the third saliva collector of FIG. 8 after the third saliva collector has been placed in a subject's mouth, but before it has collected an adequate sample of saliva.

FIG. 11 is a side elevational view in cross-section of the third saliva collector of FIG. 8 after the third saliva collector has collected an adequate sample of saliva.

FIG. 12 is a perspective view of the third container of FIG. 7 and the third saliva collector of FIG. 8 after the third saliva collector has collected an adequate sample of saliva.

FIG. 23 is a perspective view of a hollow piston which includes a first open end, a second open end and a cylindrical, rubber gasket which is snugly disposed in the second end and which is slidably coupled to the fourth container of FIG. 13.

FIG. 24 is partial longitudinal view in cross-section of the hollow piston of FIG. 23 the cylindrical, rubber gasket of which has a flange and an opening into which a filter is placed for use in separating the measured sample of a saliva from the rectangular piece of filter paper.

FIG. 25 is a side elevational view of the fourth saliva sampling device of FIG. 13 and the hollow piston of FIG. 23.

FIG. 26 is a schematic drawing showing the fourth container of FIG. 13 and the hollow piston of FIG. 23 being used to press the saliva from the fourth container into hollow piston.

DESCRIPTION OF THE PREFERRED EMBODIMENT

Figure 1:
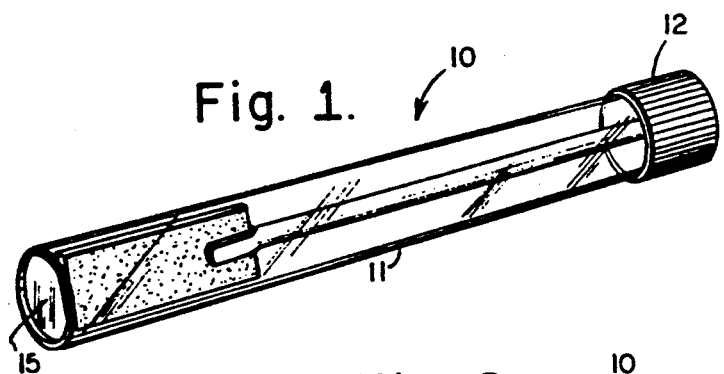
FIG. 1 is a perspective view of a first saliva sampling device which includes a first container and a first saliva collector including a first holder, a first elongated member and a first rectangular piece of filter paper, a second sample adequacy system in accordance with the principles of the first embodiment.
Figure 2:
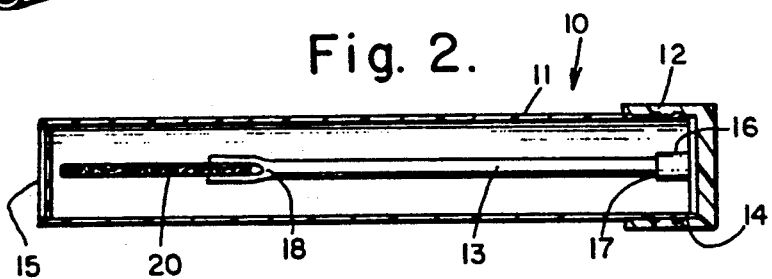
FIG. 2 is a side elevational view in cross-section of the first saliva sampling device of FIG. 1.

Referring to FIG. 1 in conjunction with FIG. 2, a first saliva sampling device 10 is used for collecting a measured sample of saliva. The first saliva sampling device 10 includes a first container 11, a cap 12 and a first saliva collector 13, which is an elongated member. The first container 11 has an open threaded end 14 and a closed end 15. The cap 12 has an inner surface 16 and is adapted to be mechanically coupled to the open threaded end 14 of the first container 11 so that the cap 12 seals the first container 11 air-tight. The first saliva collector 13 has a first end 17 and a second end 18 with the first end 17 of which being mechanically coupled to the inner surface 16 of the cap 12. The first saliva sampling device 10 also includes a first rectangular piece of filter paper 20 which is of predetermined dimensions and which is mechanically coupled to the second end 18 of the first saliva collector 13, so that a technician can collect a sample of saliva without touching the sample. Each sample of saliva is being collected wet and during the initial stages of testing of the first saliva sampling device 10 a corresponding sample of blood serum is being compared thereto.

Figure 3:
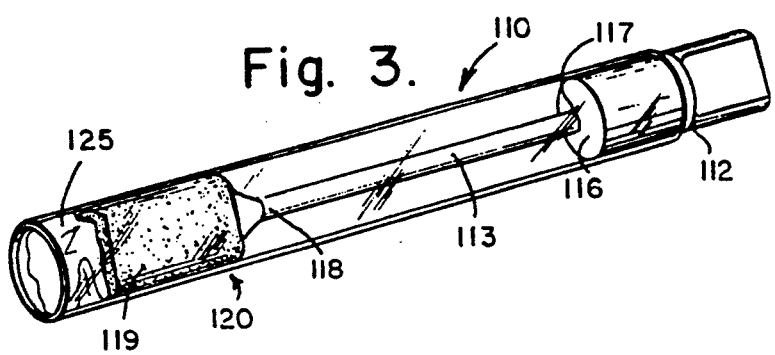
FIG. 3 is a perspective view of a second saliva sampling device which includes a second container and a second saliva collector including a second holder, a second elongated member and a second rectangular piece of filter paper in accordance with the principles of the second embodiment.
Figure 4:
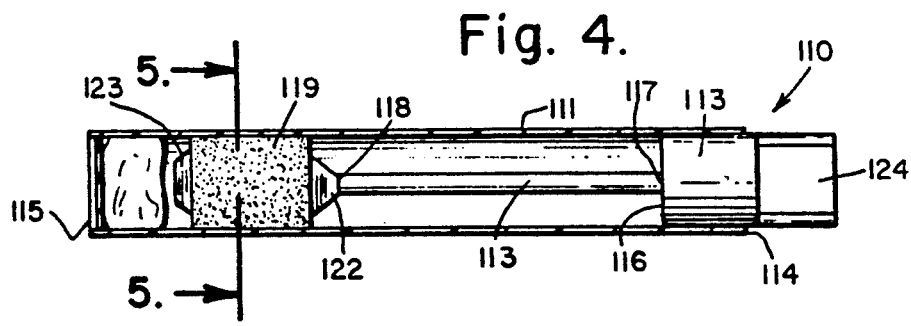
FIG. 4 is a side elevational view in cross-section of the second saliva sampling device of FIG. 3.

Referring to FIG. 3 in conjunction with FIG. 4 a second saliva sampling device 110 is used for collecting a measured sample of saliva. The second saliva sampling device 110 includes a second container 111, a plug 112 and a second saliva collector 113, which is an elongated member. The second container 111 has an open end 114 and a closed end 115. The plug 112 has an inner surface 116 and is adapted to be slidably coupled to the open end 114 of the second container 111. The plug 112 seals the second container 111 air-tight. The second saliva collector 113 has a first end 117 and a second end 118. The first end 117 of the second saliva collector 113 is mechanically coupled to the inner surface 116 of the plug 112.

Figure 5:
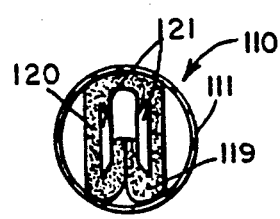
FIG. 5 is an end view in cross-section of the second saliva sampling device of FIG. 3 taken along line 5—5 of FIG. 4.
Figure 6:
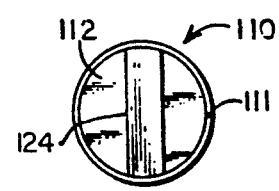
FIG. 6 is a top plan view of the second saliva sampling device of FIG. 3.

Referring to FIG. 3 in conjunction with FIG. 4 and FIG. 5 the second saliva sampling device 110 also includes a second rectangular piece of filter paper 119 of predetermined dimensions and a rectangular paddle assembly 120. The rectangular paddle assembly 120 includes two parallel and contiguous flat plates 121 each of which has a first end 122 and a second end 123 and which are joined together at their first ends 122 and mechanically coupled to the second end 118 of the second saliva collector 113. The second rectangular piece of filter paper 119 is mechanically coupled to the rectangular paddle assembly 120 so that a technician can collect the measured sample of saliva without touching the sample. The second saliva sampling device 110 further includes a labeling mechanism 124 and a dessican 125. The labeling mechanism 124 labels the second container 111 with the name of the patient and the date when the measured sample of saliva was taken. The dessican 125 removes the moisture content from the collected sample of saliva. The second saliva sampling device 110 may also include a mailer which is used to transport the collected sample of saliva to a clinical laboratory for processing and analysis.

Referring to FIG. 7 in conjunction with FIG. 8 and FIG. 9 a third saliva sampling device 210 includes a cylinder 211, a holder 212, a third saliva collector 213 and a first sample adequacy system 214. The cylinder 211 has an open end 215 and a closed end 216. The first sample adequacy system includes a solution 217 which is contained in the cylinder 211 at a liquid level and a label 218 which has a bottom edge and which is attached to the cylinder 211. The bottom edge 219 of the label 218 is disposed adjacent to the liquid level of the solution 217. The saliva collector 213 is a rectangular piece of filter paper 220 which is fixed to the holder 212. The saliva collector 213 collects a sample of saliva. The first sample adequacy system 214 determines that the collected sample of saliva is an adequate sample when the saliva collector 213 is placed in the cylinder 211, if the liquid level of the solution 217 does not drop below the bottom edge 219 of the label 218.

Referring to FIG. 8 in conjunction with FIG. 9 the third saliva collector 213 is shown before the third saliva collector 213 has been placed in a subject's mouth.

Referring to FIG. 8 in conjunction with FIG. 9 the third saliva collector 213 is shown before the third saliva collector 213 has been placed in a subject's mouth.

Referring to FIG. 11 the third saliva collector 213 is shown after the third saliva collector 213 has collected an adequate sample of saliva.

Referring to FIG. 12 after the third saliva collector 213 has collected an adequate sample of saliva, the third saliva collector 213 is placed in the container 211 if the liquid level of the solution 217 does not drop below the bottom edge 219 of the label 218 then the sample of saliva is adequate. If the liquid level of the solution 217 drops below the bottom edge 219 of the label 218 then the sample of saliva is not adequate.

Figure 13:
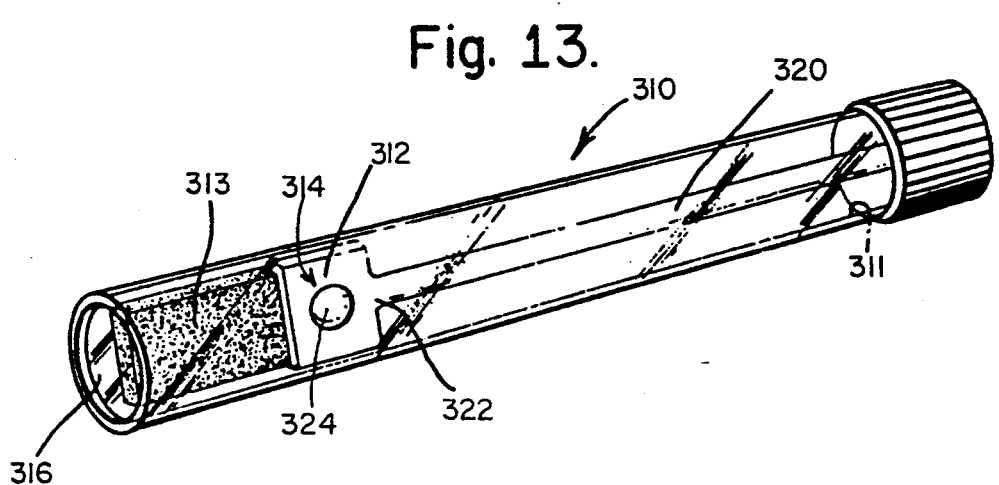
FIG. 13 is a perspective view of a fourth saliva sampling device which includes a fourth container, a fourth saliva collector including a fourth holder, a fourth elongated member, a fourth rectangular piece of filter paper and a second sample adequacy system in accordance with the principles of the fourth embodiment.
Figure 14:
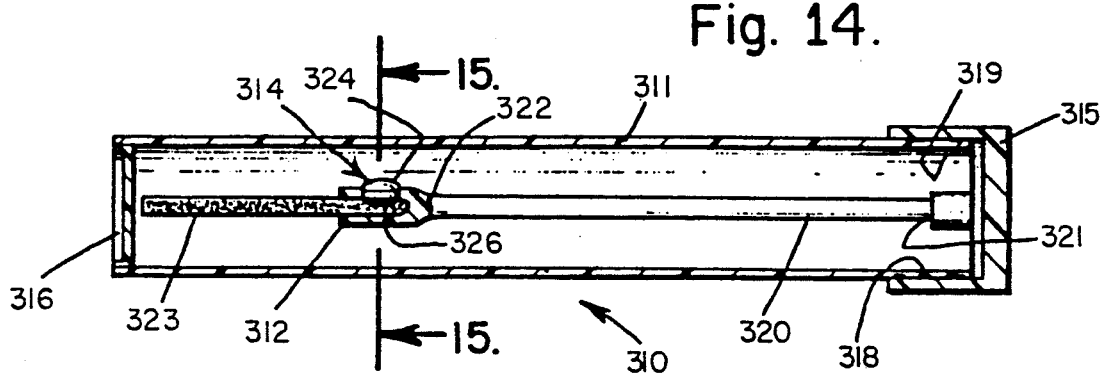
FIG. 14 is a longitudinal view in cross-section of the fourth saliva sampling device of FIG. 13.
Figure 15:
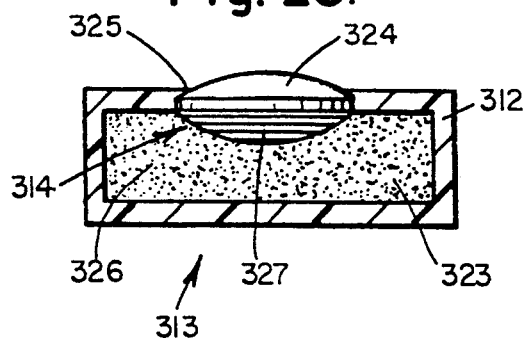
FIG. 15 is a cross-sectional view of the fourth saliva collector of the fourth saliva sampling device of FIG. 13 taken along line 15—15 of FIG. 14 showing the second sample adequacy system before the fourth saliva collector has been placed in a subject's mouth.

Referring to FIG. 13 in conjunction with FIG. 14 a fourth saliva sampling device 310 is used for collecting a measured sample of saliva. The fourth saliva sampling device 310 includes a cylinder 311, a holder 312, a fourth saliva collector 313 and a second sample adequacy system 314. The cylinder 311 has an open threaded end 315 and a closed end 316. A solution may be contained in the cylinder 311. A cap 318 has an inner surface 319 and is coupled to the open threaded end 315 of the cylinder 311 so that the cap 318 seals the cylinder 311 air-tight. An elongated member 320 has a first end 321 and a second end 322. The first end 321 of the elongated member is coupled to the inner surface 319 of the cap 318. The holder 312 is coupled to the second end 322 of the elongated member 319. A rectangular piece of filter paper 323 is of predetermined dimensions and is mechanically coupled to the holder 312 so that a technician can collect a sample of saliva without touching the sample. The second sample adequacy system 314 includes a plastic lens 324 and a hole 325 in the top surface of the holder 312 into which the plastic lens 324 is disposed. The top portion 326 of the rectangular piece of filter paper 323 is treated with a chemical reagent 327 which reacts with saliva by changing its color from a first color to a second color.

Figure 16:
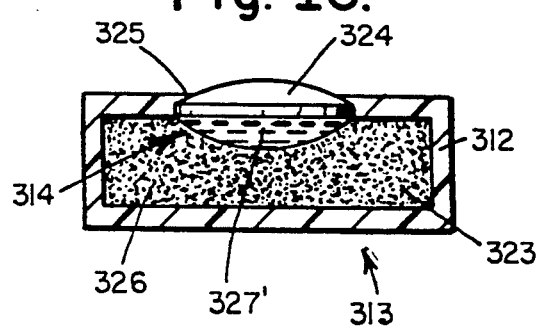
FIG. 16 is a cross-sectional view of the fourth saliva collector of FIG. 13 taken along line 15—15 of FIG. 14 showing the second sample adequacy system after the fourth saliva collector has collected an adequate sample of saliva.
Figure 17:
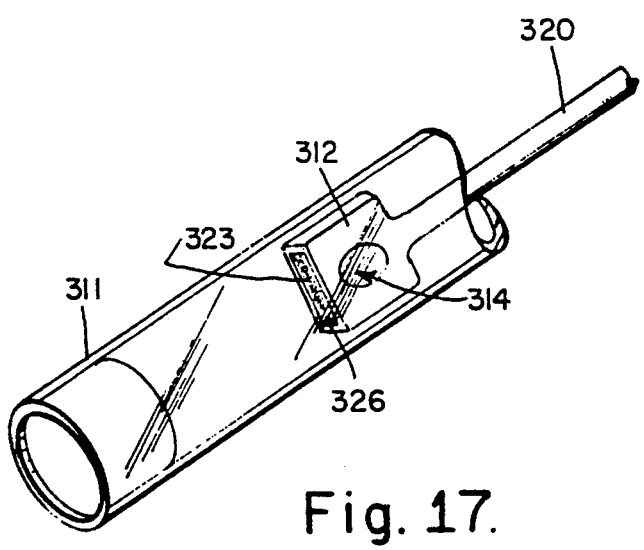
FIG. 17 is a partial perspective view of the fourth saliva sampling device of FIG. 13 in which the fourth rectangular piece of filter paper has separated from the fourth saliva collector.

Referring to FIG. 13 in conjunction with FIG. 14, FIG. 16 and FIG. 17 when a adequate amount of saliva has been collected the saliva in the rectangular piece of filter paper 323 will reach the chemical reagent 327' and change its color, e.g. from blue to clear.

Each sample of saliva will be collected wet and during the initial stages of testing of the fourth saliva sampling device 310 a corresponding sample of blood serum is being compared thereto. Once an adequate amount of saliva has been collected the saliva the holder 312 and the rectangular piece of filter paper 320 are placed into the cylinder 311 and shaken vigorously enough to separate the rectangular piece of filter paper 323 from the holder 312.

Figure 18:
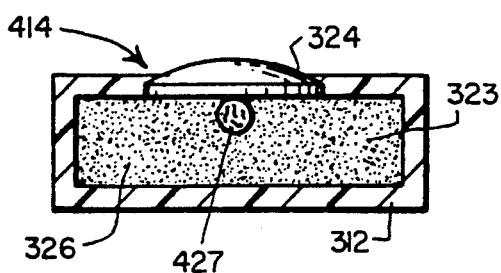
FIG. 18 is a cross-sectional view of a fifth saliva collector of a fifth saliva sampling device which includes a third sample adequacy system in accordance with the principles of the fifth embodiment showing the third sample adequacy system before the fifth saliva collector has been placed in a subject's mouth.
Figure 19:
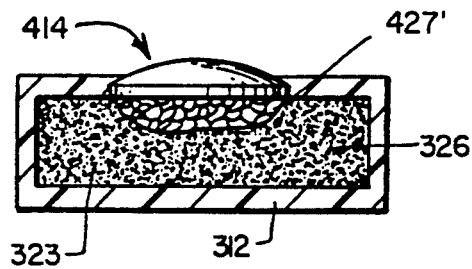
FIG. 19 is a cross-sectional view of the fifth saliva collector of FIG. 18 showing the third sample adequacy system after the fifth saliva collector has collected an adequate sample of saliva.

Referring to FIG. 13 in conjunction with FIG. 14, FIG. 18 and FIG. 19 a third sample adequacy system 414 includes the plastic lens 324 and the hole 325 in the top surface of the holder 312 into which the plastic lens 324 is disposed. The top portion 326 of the rectangular piece of filter paper 323 has a compressed sponge 427 which expands which it comes in contact with saliva. When an adequate amount of saliva has been collected the saliva in the rectangular piece of filter paper 323 will reach the compressed sponge 427' and expand it.

Figure 20:
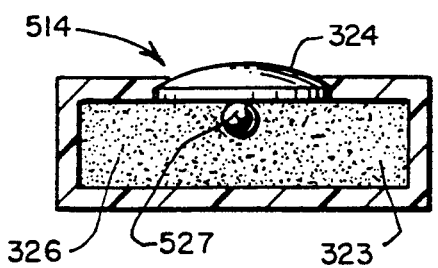
FIG. 20 is a cross-sectional view of a sixth saliva collector of a sixth saliva sampling device which includes a fourth sample adequacy system in accordance with the principles of the sixth embodiment showing the fourth sample adequacy system before the sixth saliva collector has been placed in a subject's mouth.
Figure 21:
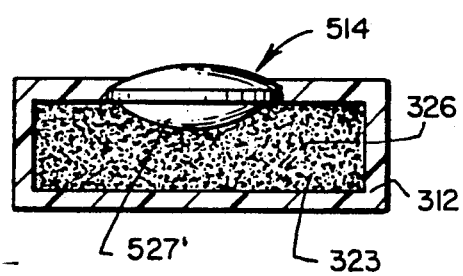
FIG. 21 is a cross-sectional view of the sixth saliva collector of FIG. 17 showing the fourth sample adequacy system after the sixth saliva collector has collected an adequate sample of saliva.

Referring to FIG. 13 in conjunction with FIG. 14, FIG. 20 and FIG. 21 a fourth sample adequacy system 514 includes the plastic lens 324 and the hole 325 in the top surface of the holder 312 into which the plastic lens 324 is disposed. The top portion 326 of the rectangular piece of filter paper 323 has an expandible polymeric bead 527 which expands which it comes in contact with saliva. When an adequate amount of saliva has been collected the saliva in the rectangular piece of filter paper 323 will reach the expandible polymeric bead 527' and expand it.

Figure 22:
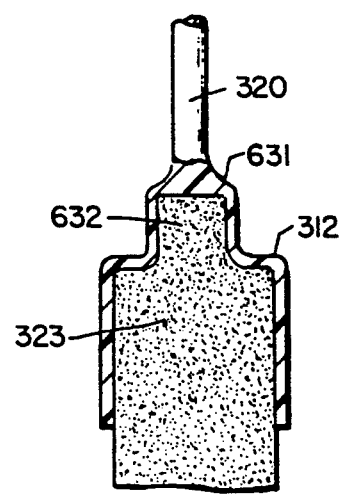
FIG. 22 is a side elevational view in cross-section of a seventh saliva collector of a seventh saliva sampling device which includes a fifth sample adequacy system in accordance with the principles of the seventh embodiment showing the fifth sample adequacy system.

Referring to FIG. 22 the holder 311 has a tab 631 on its top surface adjacent to the second end 322 of the elongated member 320. The corresponding top portion 632 of the rectangular piece of filter paper 323 may either be treated with the chemical reagent 327 or have either the compressed sponge 427 or the expandible polymeric bead 527 disposed therein.

Referring to FIG. 23 in conjunction with FIG. 24, FIG. 25 and FIG. 26 a separating device 640 includes a hollow piston 641, which has a first open end 642 and a second open end 643, and a cylindrical, rubber gasket 644 which is snugly disposed in the second end 643. The cylindrical, rubber gasket 644 is slidably coupled to the cylinder 311 of the fourth saliva sampling device 310. The cylindrical, rubber gasket 644 has a flange 645 and an opening 646 into which a filter 647 is placed for use in separating the measured sample of saliva from the rectangular piece of filter paper 323. The hollow piston 40 is used to press the saliva from the cylinder 311 into the hollow piston 641.

U.S. Pat. No. 4,895,808 teaches a test tube and tube-like adsorption column. The sample to be analyzed is prepared in solution and placed in the test tube. The tube-like adsorption column which has a seal and a valve member is forcefully fed into the test tube to force solutions through the valve member into the column and through a filter.

From the foregoing it can be seen that a sample adequacy system for use in a saliva sampling device has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:
1. A saliva sampling device comprising:
    a. a holder;
    b. a piece of filter paper which has a first portion and a second portion and which selectively receives a sample of saliva, said first portion of said piece of filter paper being disposed within and coupled to said holder enclosed thereby so that said second portion of said piece of filter paper is exposed; and
    c. an indicator activated by a preselected amount of a sample of saliva and disposed on said first portion of said piece of filter paper so that said indicator does not interfere with the collection of said sample of saliva whereby when said second portion of said piece of filter paper is inserted into a test subject's mouth saliva fluidly couples said second portion of said piece of filter paper to said indicator through said first portion of said piece of filter paper, wherein said indicator is selected from the group consisting of a compressed sponge and an expandable polymeric bead, said indicator expanding when contacted by the saliva after an adequate sample has been collected.

2. A saliva sampling device according to claim 1, said holder has a top surface with a hole and said indicator further comprises a plastic lens which is disposed in said hole of said top surface of said holder over said indicator.

* * * * *